(12) United States Patent
Jackson et al.

(10) Patent No.: US 9,198,877 B2
(45) Date of Patent: Dec. 1, 2015

(54) TRANSDERMAL SYSTEMS CONTAINING MULTILAYER ADHESIVE MATRICES TO MODIFY DRUG DELIVERY

(75) Inventors: Kristin Jackson, Enosburg Falls, VT (US); Kenneth J. Miller, St. Albans, VT (US)

(73) Assignee: Mylan Pharmaceuticals, Inc., Morgantown, WV (US)

( * ) Notice: Subject to any disclaimer, the term of this patent is extended or adjusted under 35 U.S.C. 154(b) by 0 days.

(21) Appl. No.: 13/129,638

(22) PCT Filed: Nov. 17, 2009

(86) PCT No.: PCT/US2009/064804
§ 371 (c)(1),
(2), (4) Date: Dec. 13, 2011

(87) PCT Pub. No.: WO2010/057189
PCT Pub. Date: May 20, 2010

(65) Prior Publication Data
US 2012/0078204 A1    Mar. 29, 2012

Related U.S. Application Data

(63) Continuation of application No. 12/272,706, filed on Nov. 17, 2008, which is a continuation-in-part of application No. PCT/US2005/005223, filed on Feb. 18, 2005, which is a continuation-in-part of application No. 10/795,584, filed on Mar. 9, 2004, now abandoned.

(51) Int. Cl.
*A61K 9/70*     (2006.01)
*A61F 13/00*    (2006.01)

(52) U.S. Cl.
CPC ............. *A61K 9/7092* (2013.01); *A61K 9/7053* (2013.01); *A61K 9/7061* (2013.01);

(Continued)

(58) Field of Classification Search
CPC .................................. A61K 9/70; A61F 13/02
USPC ................... 604/289, 290; 424/443, 447–449
See application file for complete search history.

(56) References Cited

U.S. PATENT DOCUMENTS 4,552,751 A    11/1985   Inaba et al.
4,666,441 A     5/1987   Adriola et al.

(Continued)

FOREIGN PATENT DOCUMENTS

EP    0033615 A2    8/1981
EP    0259136 A2    3/1988

(Continued)

OTHER PUBLICATIONS

Japanese Patent Application No. 2007-502827: Official Action from the Japanese Patent Office from Sep. 26, 2012, in English.

(Continued)

*Primary Examiner* — Melanie Hand
(74) *Attorney, Agent, or Firm* — Paul Zagar (Blank Rome, LLP)

(57) ABSTRACT

A transdermal drug-containing dosage unit comprises: a backing layer substantially impervious to the drug to be delivered transdermally; a first polymeric adhesive matrix, in contact with the backing layer, having dispersed therein the drug and having a first delivery profile of the drug; a second polymeric adhesive matrix, in contact with said first polymeric adhesive matrix, having dispersed therein the drug and having a second delivery profile of the drug, wherein said second delivery profile is different from said first delivery profile; and a release liner in contact with the second polymeric adhesive matrix. The first polymeric adhesive matrix can release the drug more quickly or more slowly than the second polymeric adhesive matrix. Through the selection of the two matrices, the delivery profile of the drug through the skin can be selectively modified and controlled.

19 Claims, 9 Drawing Sheets

(52) U.S. Cl.
CPC ....... *A61K9/7069* (2013.01); *A61F 2013/0071* (2013.01); *A61F 2013/00646* (2013.01); *A61F 2013/00906* (2013.01)

(56) References Cited

U.S. PATENT DOCUMENTS

| | | | |
|---|---|---|---|
| D296,006 S | 5/1988 | Asche | |
| 4,769,028 A | 9/1988 | Hoffmann et al. | |
| 4,844,903 A | 7/1989 | Seth | |
| 4,877,618 A | 10/1989 | Reed | |
| 4,882,377 A | 11/1989 | Sweet et al. | |
| 4,883,669 A | 11/1989 | Chien et al. | |
| 4,906,169 A | 3/1990 | Chien et al. | |
| 4,906,463 A | 3/1990 | Cleary et al. | |
| 4,906,475 A | 3/1990 | Kim | |
| 4,915,950 A | 4/1990 | Miranda et al. | |
| 4,978,532 A | 12/1990 | El-Rashidy | |
| 4,997,655 A | 3/1991 | Nagy et al. | |
| 5,023,084 A | 6/1991 | Chien et al. | |
| 5,066,494 A | 11/1991 | Becher | |
| 5,176,915 A | 1/1993 | Hoffmann | |
| 5,230,898 A | 7/1993 | Horstmann et al. | |
| 5,232,702 A | 8/1993 | Pfister et al. | |
| 5,284,660 A | 2/1994 | Lee et al. | |
| 5,300,299 A | 4/1994 | Sweet et al. | |
| 5,350,581 A | 9/1994 | Kochinke | |
| 5,370,924 A | 12/1994 | Kochinke | |
| 5,456,745 A | 10/1995 | Roreger et al. | |
| 5,482,988 A | 1/1996 | Ulman et al. | |
| 5,562,917 A | 10/1996 | Durif et al. | |
| 5,582,836 A | 12/1996 | Carli et al. | |
| 5,626,866 A | 5/1997 | Ebert et al. | |
| 5,656,286 A | 8/1997 | Miranda et al. | |
| 5,686,099 A | 11/1997 | Sablotsky et al. | |
| 5,902,433 A | 5/1999 | Becher et al. | |
| 5,958,446 A | 9/1999 | Miranda et al. | |
| 6,337,086 B1 | 1/2002 | Kanios et al. | |
| 6,730,318 B2 | 5/2004 | Quan et al. | |
| 6,791,003 B1 | 9/2004 | Choi et al. | |
| 6,893,655 B2 | 5/2005 | Flanigan et al. | |
| 2001/0009673 A1 | 7/2001 | Lipp et al. | |
| 2002/0119187 A1 | 8/2002 | Cantor et al. | |
| 2002/0187181 A1 | 12/2002 | Godbey et al. | |
| 2004/0013716 A1* | 1/2004 | Gale et al. | 424/449 |
| 2004/0101551 A1 | 5/2004 | Selzer | |
| 2004/0265363 A1 | 12/2004 | Hille et al. | |
| 2005/0202073 A1 | 9/2005 | Jackson et al. | |

FOREIGN PATENT DOCUMENTS

| | | |
|---|---|---|
| EP | 0301424 A2 | 2/1989 |
| EP | 0484543 A1 | 5/1992 |
| EP | 1188436 A2 | 3/2002 |
| JP | S57-7413 A | 1/1982 |
| JP | 61-267510 A | 11/1986 |
| JP | 63-307814 A | 12/1988 |
| JP | H06205839 A | 7/1994 |
| JP | 04-504109 A | 7/1997 |
| JP | H10203713 A | 8/1998 |
| JP | 2003-511425 A | 3/2003 |
| JP | 2003-104874 A | 4/2003 |
| WO | WO 90/06736 A1 | 6/1990 |
| WO | WO 95/24172 A1 | 9/1995 |
| WO | WO 01/13899 A2 | 3/2001 |
| WO | 01/26705 A2 | 4/2001 |
| WO | 0130316 A2 | 5/2001 |
| WO | 0137770 A1 | 5/2001 |
| WO | 0226217 A2 | 4/2002 |
| WO | 03/077890 A1 | 9/2003 |
| WO | 03097020 A1 | 11/2003 |
| WO | WO 2005/025549 | 3/2005 |
| WO | 2005091852 A2 | 10/2005 |

OTHER PUBLICATIONS

U.S. Appl. No. 12/979,120: Non-Final Office Action dated Jan. 29, 2013.
L. Margetts et al., "Transdermal drug delivery: principles and opioid therapy," Critical Care & Pain, vol. 7, No. 5, 2007, pp. 171-176.
Office Action, mailed Oct. 6, 2014, which issued during the prosecution of U.S. Appl. No. 12/272,706.
Notice of Allowance mailed Jul. 18, 2014, which issued during the prosecution of U.S. Appl. No. 12/979,120.
Notification of Reason for Rejection, mailed Oct. 1, 2014, which issued during the prosecution of Japanese Patent Application No. 2007-502827.
Notice of Allowability, mailed Nov. 4, 2014, which issued during the prosecution of U.S. Appl. No. 12/979,120.
U.S. Office Action issued in related U.S. Appl. No. 12/272,706 dated Mar. 23, 2015.
Japanese Notice of Allowance issued in Japanese Application No. 2007-502827 dated Feb. 19, 2015.
Office Action, mailed Feb. 14, 2014, which issued during the prosecution of U.S. Appl. No. 12/979,120.
Office Action, mailed Mar. 28, 2014, which issued during the prosecution of U.S. Appl. No. 12/272,706.
DURO-TAK® Transdermal Pressure Sensitive Adhesives Product Selection Guide.
H. J. Yoon et al., Transdermal Fentanyl Matrix Patch—Evaluation of a parallel binary matrix system—published on Apr. 19, 2000.
Notice of Opposition filed Apr. 7, 2014 against EP Patent No. 1737406 B1.
Notice of Opposition filed Apr. 10, 2014 against EP Patent No. 1737406 B1.
European Patent Application No. 05713798: EPO Communication Pursuant to Rule 114(2) EPC, Feb. 12, 2009, Third Party Observations.
PCT Application No. PCT/US2009/64804: International Search Report (2 pages).
Rote Liste 2002; Arzneimittelverzeichnis fur Deutschland (einschlieBlich EU-Zulassungen und bestimmter Medizinprodukte) (HSG: Rote Liste Service GmbH, Frankfurt/Main), published 2002, 36 pages.
Satas (editor), "Silicone Pressure Sensitive Adhesives," Handbook of Pressure-Sensitive Adhesive Technology, 2nd Editition, Van Nostrand Reinhold, pp. 514-517 (1989).
U.S. Appl. No. 10/795,584: Non-Final Office Action, dated Jul. 25, 2008.
U.S. Appl. No. 10/795,584: Final Office Action, dated Apr. 21, 2009.
U.S. Appl. No. 10/795,584: Non-Final Office Action, dated Feb. 2, 2010.
U.S. Appl. No. 10/795,584: Final Office Action, dated Jul. 15, 2010.
Office Action, mailed Dec. 8, 2014, which issued during the prosecution of U.S. Appl. No. 12/979,120.

* cited by examiner

TRANSDERMAL SYSTEMS CONTAINING MULTILAYER ADHESIVE MATRICES TO MODIFY DRUG DELIVERY

CROSS-REFERENCE TO RELATED APPLICATIONS

This application claims priority to U.S. patent application Ser. No. 10/795,584 filed on Mar. 9, 2004 and published as U.S. Pat. Pub. 2005/0202073, which is herein incorporated by reference in its entirety. This application also claims priority to PCT Application PCT/US2005/005223 filed on Feb. 18, 2005 and published as WO 2005/091852, which is herein incorporated by reference in its entirety.

BACKGROUND OF THE INVENTION

This invention relates to transdermal, pressure sensitive, adhesive delivery systems for the delivery of an agent, such as a drug, through the skin. More specifically, this invention is directed to such systems which comprise multilayer adhesive matrices.

A well-known method of delivering certain drugs in a controlled manner over time is through the use of a transdermal composition, such as a pressure sensitive adhesive containing the drug. Known delivery systems involve the incorporation of the desired drug into a carrier, such as a polymeric matrix and/or pressure sensitive adhesive formulation. Problems encountered with such delivery systems have included insufficient control over the rate and duration of the transdermal absorption, and a variety of compositions have been developed in efforts to maximize control of the release of a desired drug and the efficacy of the delivery unit.

Although a number of commercially useful transdermal delivery systems have been produced, further improvements are sought.

SUMMARY OF THE INVENTION

In accordance with the present invention, a transdermal drug-containing dosage unit comprises:

a) a backing layer substantially impervious to the drug to be delivered transdermally;

b) a first polymeric adhesive matrix, in contact with at least a portion of the backing layer, having dispersed therein the drug and having a first initial delivery profile of the drug;

c) a second polymeric adhesive matrix, in contact with at least a portion of said first polymeric adhesive matrix, having dispersed therein the drug and having a second delivery profile of the drug, wherein said second delivery profile is different from said first delivery profile; and d) a removable release liner in contact with at least a portion of the second polymeric adhesive matrix.

The invention further comprises a method for administering a drug transdermally to an individual in need of such administration, comprising applying to the skin of the individual a transdermal dosage unit comprising:

a) a backing layer substantially impervious to the drug to be delivered transdermally;

b) a first polymeric adhesive matrix, in contact with at least a portion of the backing layer, having dispersed therein the drug and having a first initial delivery profile of the drug; and c) a second polymeric adhesive matrix, in contact with at least a portion of said first polymeric adhesive matrix, having dispersed therein the drug and having a second delivery profile of the drug, wherein said second delivery profile is different from said first delivery profile.

The first polymeric adhesive matrix can release the drug more quickly or more slowly than the second polymeric adhesive matrix. Through the selection of the two matrices, the delivery profile of the drug through the skin can be selectively modified and controlled to an extent not possible with delivery devices which comprise only a single adhesive matrix.

If desired, the compositions further can contain or employ other ingredients known for use in pressure sensitive adhesives, including crosslinking agents, plasticizers, tackifiers, anti-oxidants and excipients or penetration enhancers.

BRIEF DESCRIPTION OF THE FIGURES

FIG. 3a shows the in vitro transdermal data and FIG. 3b shows the polynomial correlation for a fast adhesive monolith and several bi-layer matrices in accordance with this invention.

FIG. 4a shows the 3-D cumulative delivery correlation and FIG. 4b shows the 3-D flux correlation for slow skin-contact adhesives bi-layers.

FIG. 5a shows the in vitro transdermal data and FIG. 5b shows the polynomial correlation for several bi-layer matrices in accordance with this invention.

FIG. 6a shows the 3-D cumulative delivery correlation and FIG. 6b shows the 3-D flux correlation for slow skin-contact adhesive bi-layers.

DETAILED DESCRIPTION OF THE INVENTION

Figure 1:
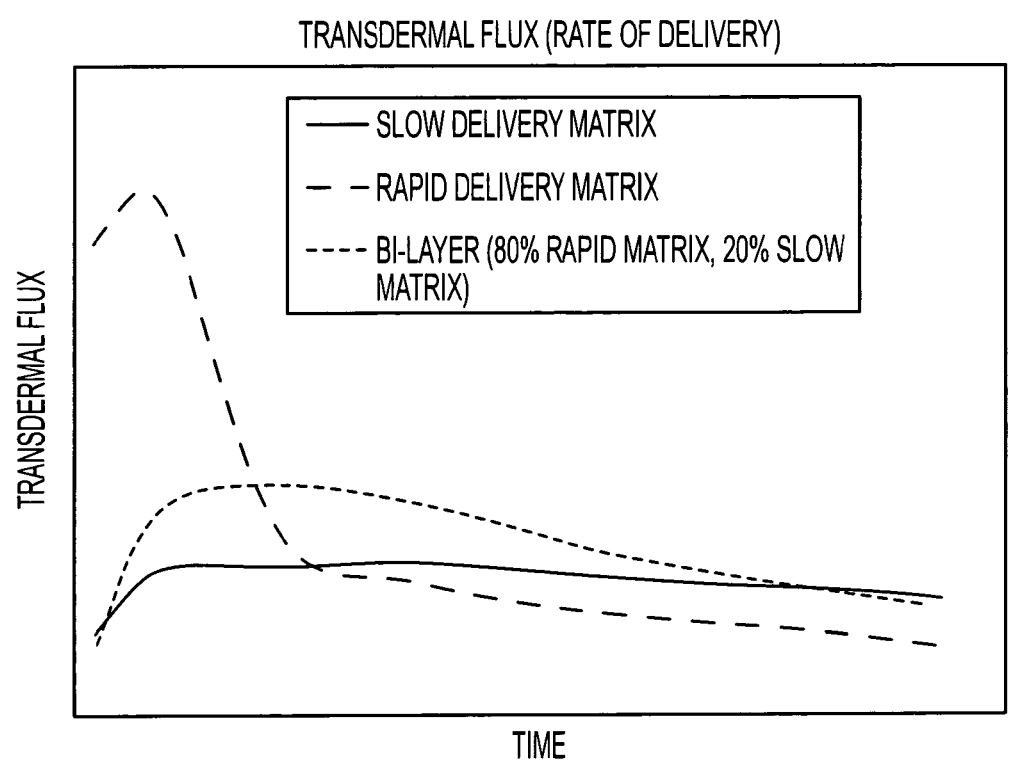
FIG. 1 is a graph showing the transdermal flux (rate of delivery) of three matrices, including a bi-layer matrix in accordance with this invention.

This invention is directed to dermal compositions suitable for the delivery of a drug through the skin. The compositions allow for very controlled delivery of the drug through the unique combination of two or more different adhesive matrices which can be selected and layered to provide a desired drug delivery profile.

Specifically, compositions of the present invention comprise:

a) a backing layer substantially impervious to the drug to be delivered transdermally;

b) a first polymeric adhesive matrix, in contact with at least a portion of the backing layer, having dispersed therein the drug and having a first delivery profile of the drug;

c) a second polymeric adhesive matrix, in contact with a portion of said first polymeric adhesive matrix, having dispersed therein the drug and having a second delivery profile of the drug; and d) a removable release liner in contact with at least a portion of the second polymeric adhesive matrix.

The first and second polymeric adhesive matrices in a two matrix composition also will be referred to as the anchor adhesive layer and the skin contact adhesive layer, respectively. They are selected such that there is a significant difference in the rate of drug delivery from each layer. In addition, the two adhesives also can be selected such that there is a significant difference in one or more other physical characteristics, such as the solubility, miscibility or stability of the drug or desired excipients, in each of the two layers, which can further affect the delivery of the drug from the composition and through the skin of the person wearing the composition. As used herein, "significant difference" means a difference in drug delivery of at least about 10%-100%, preferably at least about 15%-60%, between the two adhesive matrices or layers. The desired difference in drug delivery rates between the two layers can be achieved simply through the selection of the two adhesive matrices or through the selection of the adhesive for each matrix in combination with the choice of relative thickness of each layer.

The first and second adhesive matrices can be selected such that the rate of drug delivery initially is faster from the second matrix, or skin contact layer, than it is from the first matrix, or anchor layer. In such instances, there will be an initial burst, or spike, of drug delivered through the skin of the wearer, followed by a slower and more steady release of the drug. Alternatively, the adhesive matrices can be selected such that the rate of drug delivery initially is faster from the first matrix, or anchor layer, than it is from the second matrix, or skin contact layer. Such a system allows for the tuning of the delivery profile depending upon the thickness of the two layers. Specifically, the slower delivering adhesive layer contacting the skin controls the delivery through the skin and modulates the faster delivering adhesive layer's tendency to deliver the drug rapidly. In such instances, there will be a continuous drug delivery, perhaps with a "burst" in delivery at a specific time post-application, depending upon the thickness and composition of the matrices and the drug concentration. For instance, the burst could be accounted for by a release of drug and components by the anchor layer having a driving force so great as to overcome any rate limiting properties that the skin contact layer may have. Such a release pattern is useful, for example, in delivering drugs to the body to mimic a circadian rhythm (e.g., testosterone).

The rate of release from an adhesive matrix can change over the course of its functional lifespan. Often, this is caused by the absorption of water or other components from the surface of the skin of the wearer. Alternatively, one can incorporate into the skin contact matrix an exhaustible penetration retardant or load the skin contact matrix with solid drug crystals to impair initial delivery of the drug through the skin.

In one embodiment of this invention, the composition comprises more than two adhesive matrices, such as three or four or five adhesive matrices. For example, a composition could comprise one or more additional adhesive matrices sandwiched in between the adhesive matrix which is in contact with the backing layer, and the adhesive matrix which is in contact with the release liner. An advantage to including three or more matrices is having increased ability to control the rate of delivery either through the use of the different layers or by adding different excipients to the different layers to change or control the rate of delivery. Other advantages include increased chemical stability, processing, cosmetic or physical (improved wear) advantages. If there are more than two adhesive matrixes in a composition, the initial rate of delivery of the drug from one of the matrices is different from that from at least one of the other matrices. In one embodiment, the initial rate of drug delivery in each matrix is different from that of each other matrix.

The adhesives used in the compositions, or unit dosage forms, of the present invention are those which are tacky or sticky to the touch and which typically adhere to a substrate, such as the skin, upon the application of mild pressure. They therefore often are referred to as pressure sensitive adhesives.

The choice for each adhesive matrix layer can be made from any pressure sensitive adhesives conventionally used in transdermal delivery devices, provided that the two materials chosen have significantly different drug delivery rates. In one preferred embodiment, one matrix comprises an acrylic adhesive and the other matrix comprises a silicone adhesive. In this combination, the acrylic adhesive has the relatively slow delivery characteristics; the silicone adhesive has the more rapid delivery characteristics. In a second preferred embodiment, one matrix comprises an acrylic adhesive and the other comprises a polyisobutylene adhesive. In this embodiment, the acrylic adhesive again has the relatively slow delivery characteristics; the polyisobutylene adhesive delivers the drug more rapidly.

If the composition comprises three adhesive matrices, it can comprise, for example, an acrylic adhesive layer sandwiched between two silicone adhesive layers, or a silicone adhesive layer in between two acrylic adhesive layers. Alternatively, each layer could have a different polymer, such as a silicone, polyisobutylene, and acrylate adhesive multilayer system. The choice of adhesive for each layer will be determined by the delivery profile desired for the final composition.

Suitable silicone adhesives include pressure sensitive adhesives made from silicone polymer and resin. The polymer to resin ratio can be varied to achieve different levels of tack. Specific examples of useful silicone adhesives which are commercially available include the standard BIOPSA® series (7-4400, 7-4500 and 7-4600 series) and the amine compatible (endcapped) BIOPSA® series (7-4100, 7-4200 and 7-4300 series) manufactured by Dow Corning. Preferred adhesives include BIO-PSA® 7-4202, BIO-PSA® 7-4301, BIO-PSA® 7-4302, BIO-PSA® 7-4501, BIO-PSA® 7-4502 and BIO-PSA® 7-4602.

Suitable polyisobutylene adhesives are those which are pressure sensitive and have suitable tack. The polyisobutylene can comprise a mixture of high and low molecular weight polyisobutylenes. Specifically, high molecular weight polyisobutylenes are those with a molecular weight of at least 1,000,000. Low molecular weight polyisobutylenes are those with a molecular weight of at least 100 but less than 1,000, 000. Desirably, the high molecular weight polyisobutylene comprise between about 20 and 80% by weight of the total polyisobutylene, preferably between about 40% and 50%, most preferably about 45%, and the low molecular weight polyisobutylene comprises between about 80% and 20% by weight of the total polyisobutylene, preferably between about 50% and 60%, most preferably about 55%. A specific example of a useful polyisobutylene is one which comprises 45% high molecular weight polymer (~1,250,000) and 55% low molecular weight polymer (~44,000) at approximately 25% solids in n-heptane.

Useful acrylic polymers include various homopolymers, copolymers, terpolymers and the like of acrylic acids. They include copolymers of alkyl acrylates or methacrylates. Polyacrylates include acrylic acid, methacrylic acid, N-butyl acrylate, n-butyl methacrylate, hexyl acrylate, 2-ethylbutyl acrylate, isooctyl acrylate, 2-ethylhexyl acrylate, 2-ethylhexyl methacrylate, decyl acrylate, decylmethacrylate, dodecyl acrylate, dodecyl methacrylate, tridecyl acrylate, and tridecyl methacrylate. Useful acrylic adhesives include crosslinked carboxyl functional adhesives such as DURO-TAK®87-2194, non-crosslinked carboxyl functional adhesives such as DURO-TAK®87-2051, crosslinked hydroxyl functional adhesives such as DURO-TAK®87-2516, non-crosslinked hydroxyl functional adhesives such as DURO-TAK®87-2287, grafted adhesives such as DURO-TAK®87-5298 and non-functional adhesives such as DURO-TAK®87-4098. Preferred acrylic adhesives include crosslinked carboxyl functional acrylic adhesives, such as DURO-TAK® 87-2194 manufactured by National Starch and Chemical Co.

In addition to the aforementioned adhesives, other adhesives useful in compositions in accordance with this invention include other acrylate, rubber or silicone pressure adhesives, whether hotmelt, waterborne or solvent based.

In addition to the two or more adhesive layers, compositions in accordance with this invention comprise a backing and a release liner, each of which can comprise materials conventionally used in transdermal patch compositions. The material chosen for the backing is one which is flexible, impermeable to the drug, and, if desired, can be colored or labeled. The backing provides support and a protective covering for the dosage unit. Suitable backing materials include those known in the art for use with pressure sensitive adhesives. For example, the backing can comprise a polyolefin, polyester, multi-layer EVA film and polyester, polyurethane or combination thereof. A preferred backing material is MEDIFLEX® 1000, a polyolefin manufactured by Mylan Technologies, Inc.

The release liner is removed and discarded from the composition to expose the skin contact adhesive layer which functions as the means of applying the composition to the patient and through which the drug passes as it is delivered to the patient. Suitable release liners include those known in the art for use with pressure sensitive adhesive compositions. For example, the release liner can comprise a fluorosilicone coated polyester or silicone coated polyester. A preferred release liner is MEDIRELEASE® 2500, MEDIRELEASE® 2249 and MEDIRELEASE® MR2226, each manufactured by Mylan Technologies, Inc., or Scotchpak® 1022, manufactured by 3M Pharmaceuticals/D.D.S. The release liner can, however, comprise other materials, including paper or paper-containing layers or laminates, various thermoplastics, polyester films, foil liners, and the like.

Once the dosage unit forms have been prepared, they are placed in appropriate packaging for storage until they are to be applied in transdermal treatment.

The compositions of this invention possess sufficient adhesive properties that once the release liner is removed and the composition is applied to the skin the composition can remain in place for a period of time sufficient to distribute the desired amount of the drug contained therein with a low incidence of debonding.

The compositions of this invention can be made by first preparing separate adhesive blends for each layer of the dosage unit, then dissolving or suspending the drug of choice in at least one of the blends, each of which has been made by mixing a suitable solvent with the pressure sensitive adhesive of choice. The anchor layer is coated first on a release liner, dried and then laminated to the desired backing film, according to predetermined parameters, such as temperature and dwell time (line speed), which yield minimal residual solvent levels. The skin contact layer then is coated on a separate release liner and dried. The release liner is removed from the anchor layer and the adhesive side of the skin contact layer is laminated onto the adhesive side of the anchor layer so that the anchor layer is between the backing and the skin contact layer. If the drug initially is suspended or dissolved in only one of the two adhesive layers, it will, over time, equilibrate into the other adhesive layer until a common equilibrium is achieved. It may be desirable to prepare the composition with the drug initially suspended or dispersed in only one of the two adhesive layers if, for example, the other adhesive layer is prepared with a solvent which would be deleterious to the drug but which evaporates during processing (coating and drying).

If more than two layers are to be provided, the third (middle) layer is coated as a liquid onto a release liner, dried, laminated to either the adhesive side of the dried skin contact layer or the adhesive side of the dried anchor layer once the release liner has been removed from the latter, then the two parts of the dosage unit are laminated to one another as above.

Suitable solvents for use in preparing the adhesive blends include acetone, heptane, ethyl acetate, isopropanol, ethanol, hexane, toluene, xylene, 2,4-pentanedione, methanol and water.

Alternative methods for producing or achieving a transdermal delivery dosage unit in accordance with this invention may be apparent to persons skilled in the art, and such alternative methods also fall within the scope of the present invention. For example, an adhesive blend can be coated onto the backing film rather than the release liner. Alternatively, an adhesive coating can be created without using a solvent, such by heating the adhesive to its melting temperature (hot-melt adhesive). With this technique, no drying of the adhesive is required, only cooling.

There are many coating techniques for applying a continuous liquid coating onto a substrate, including using a gravure roll, reverse roll, falling film, inkjet, etc. All of these are well-known to persons of ordinary skill in the art and can be used to create pressure-sensitive adhesive layers from a solvated blend. Alternatively, a thin adhesive coating can be achieved by extrusion, in which the adhesive blend is forced through a die under pressure onto the substrate either as a continuous coating or as a printed (intermittent) pattern.

The thickness of the anchor and skin contact layers of the compositions of this invention can vary, depending upon such factors as the amount of drug to be delivered from the composition and the desired wear period. Generally, however, the skin contact layer has a thickness of between about 5 and 150 gsm, preferably between about 25 and 50 gsm. The anchor layer generally has a thickness of between about 5 and 150 gsm, preferably between about 25 and 100 gsm. Variations can be determined as a matter of routine experimentation by those of ordinary skill in the art.

The compositions of the present invention are suitable for the transdermal delivery of a wide range of drugs. The term "drugs" is intended to have its broadest interpretation as including any therapeutically, prophylactically and/or pharmacologically or physiologically beneficial active substance, or a mixture thereof, which is delivered to a living being to produce a desired, beneficial effect. More specifically, any drug which can produce a pharmacological response, localized or systemic, whether therapeutic, diagnostic, or prophylactic in nature, is within the contemplation of the present invention. Also included within the scope of the invention are bioactive agents, such as insect repellants, sun screens, cosmetic agents, etc. The drug can be provided in an amount sufficient to cure, diagnose, or treat a disease or other condition. This definition includes, but is not limited to:

1. cardiovascular drugs, such as nitroglycerin, propranolol, isosorbide dinitrate, isosorbide mononitrates, diltiazem, nifedipine, procainamide, clonidine and others, 2. androgenic steroids, such as testosterone, methyltestosterone and fluoxymesterone, 3. estrogens, such as conjugated estrogens, esterified estrogens, etropipate, 17-β estradiol, 17-β estradiol valerate, equilin, mestranol, estrone, estriol and diethylstilbestrol, 4. progestational agents, such as progesterone, 19-nor-progesterone, norethindrone, norethindrone acetate, melengestrol chloradinone, ethisterone, medroxyprogesterone acetate, hydroxyprogesterone caproate, norethynodrel, dimethisterone, ethinylestrenol, norgestrel, megestrolacetate, and ethinodiol diacetate, 5. drugs which act on the central nervous system, including sedatives, hypnotics, analgesics, anesthetics, and antianxiety agents; such as salicylic acid derivatives, opiates, opioids and the like; including chloral hydrate, benzodiazepines, naloxone, haloperidol, pentobarbitol, phenobarbitol, secobarbital, codeine, lidocaine, dibucaine, benzocaine, fentanyl, fentanyl analogs and nicotine, 6. nutritional agents, including vitamins, essential amino acids and essential fats, 7. anti-inflammatory agents, including hydrocortisone, cortisone, dexamethasone, prednisolone, prednisone, halcinonide, methylprednisolone, flurocortisone, corticosterone, paramethasone, ibuprofen, naproxen, fenoprofen, fenbufen, indoprofen, salicylic acid, methyl salicylate, sulindac, mefenamic acid, piroxicam, indonisilone and tolmetin, 8. antihistamines, such as diphenhydramine, triprolidine, chlorcyclizine, promethazine, cyclizine, chlorprenaline, terrenadine, phenylpropanolamine and chlorpheniramine, 9. miotics, such as pilocarpine, 10. dermatological agents, such as vitamins A and E, 11. anti-spamodics, including atropine, methantheline, papverine, cinnmedrine and methscopolamine, 12. anti-depressants, such as isocaboxazid, phenelzine, imipramine, amitrptyline, trimepramine, dozepin, desipramine, nortriptyline, protriptyline, amoxapine and maprotiline, 13. anti-cancer drugs, 14. anti-diabetics, such as insulin, 15. anti-estrogens or hormone agents, including tamoxifen or HCG, 16. anti-infectives, including antibiotics, anti-bacterials and anti-virals, such as tetracycline, chloramphenicol, sulfacetamide, sulfadiazine, sulfamerazine, sulfoxazole, idoxuridine, and erythromycin, 17. anti-allergenics, such as antazoline, metapyrilene, and pyrilamine, 18. anti-pyretics, including aspirin and salicylamide, 19. anti-migraine agents, including dihydroergotamine and pizotyline, 20. tranquilizers, including reserpine, chlorpromazine, and antianxiety benzodiazepines, and 21. anti-psychotic agents, including haloperidol loxapine, molindone, thiothixene, pimozide, risperidone, quetiapine fumarate, olanzapine, and/phenothiazine derivatives.

Other drugs suitable for delivery using a transdermal system can be readily determined by persons of ordinary skill in the art. In addition, pharmacologically acceptable derivatives of the drugs, such as ethers, esters, amides, acetals, salts and the like, which are suitable for transdermal administration can be used.

In a preferred embodiment, a composition of this invention comprises estradiol, a combination of estradiol and norethindrone acetate or a combination of estradiol and levonorgestrel or other progestin. Such patches are indicated for post-menopausal women as hormone replacement therapy. One or more bioactive and biocompatible derivatives of estradiol capable of being absorbed transdermally can be used in place of, or in combination with, estradiol. Derivatives of estradiol include 13- or 7-mono-esters and di-esters of estradiol, including estradiol-3,17-diacetate; estradiol-17-acetate; estradiol-3,17-valerate; estradiol-3-valerate; estradiol-17-valerate; 3-mono-17-mono- and 3,17-dipilivate esters; 3-mono-, 17-mono-, and 3,17-dipropionate esters; corresponding heptanoate and benzoate esters; ethanol estradiol; estrone; and other estrogenic steroids and derivatives which are transdermally absorbable.

Other suitable progestins include progesterone, medroxyprogesterone acetate, ethynodiol diacetate, and the like.

When estradiol is used as the sole active drug in the dosage unit, each unit typically comprises from about 0.1% to about 4.0% (w/w) estradiol. When estradiol is provided in combination with either norethindrone or levonorgestrel or other progestin, each dosage unit typically comprises about 0.1% to about 4.0% (w/w) estradiol and about 0.1% to about 20% of the progestin. These ranges are intended only as guidelines; the actual amount of drug provided depends upon the choice of adhesive for the skin contact and anchor layers, the amount of drug desired to be delivered transdermally to the patient within a certain period of time, and the rate at which the drug can permeate through the skin of the person wearing the dosage unit or patch.

In one specific embodiment of this invention, a transdermal dosage unit comprises a silicone skin contact layer of about 25 gsm (grams/m$^2$) and an acrylate anchor layer of about 75 gsm and contains about 1.4% (w/w) estradiol. In a second specific embodiment, a transdermal dosage unit comprises a silicone skin contact layer of about 50 gsm and an acrylate anchor layer of about 75 gsm and contains about 1.4% estradiol. In a third specific embodiment, a transdermal dosage unit comprises a silicone skin contact layer of about 25 gsm and an acrylate anchor layer of about 100 gsm, each containing about 1.4% estradiol.

In a fourth specific embodiment, a transdermal dosage unit comprises a polyisobutylene skin contact layer of about 50 gsm which contains 1.0% (w/w) estradiol and a 50 gsm anchor layer which contains about 1.4% (w/w) estradiol in an acrylate adhesive.

The amount of drug to be incorporated into the compositions of this invention vary, depending upon the drug or combination of drugs of interest, the desired therapeutic effect and the time span over which the composition will release the drug and provide therapy. As the passage of drugs through the skin often is the rate limiting step, the amount of drug chosen and the rate of release from the adhesives typically are selected so as to provide for delivery of the drug for a prolonged period of time, wherein the minimum amount of the drug in the system is based upon the rate at which it will pass through the skin in the time period for which the composition is to provide therapy. The amount of drug in the composition typically can vary from about 0.05% to about 40% by weight of the delivery device and preferably is within the range of about 0.1% to about 20% by weight, most preferably within the range of about 0.1% to about 4.0% by weight.

The drug(s) of interest can be provided in admixture with other ingredients which are compatible with the transdermal administration of the desired drug to patients. Such other ingredients include crosslinking agents, plasticizers, tackifiers, fillers, anti-oxidants, dispersing agents and excipients, such as propylene glycol.

The present invention provides the ability to tune the transdermal delivery profile (e.g., maximum flux vs. average flux) by altering layer thicknesses and without risking drug crystallization. Placing the two matrices in intimate contact at a common interface allows the drug in either matrix to equilibrate across that interface until the drug is at the same activity everywhere in the matrices. In one embodiment, the full surface area of the two matrices are in contact with each other. In another embodiment, at least 75% of the surface area both of the matrices are in contact with each other.

In one preferred embodiment, each monolith layer comprises a concentration of drug that is sub-saturated. Thus, any combination of these monoliths will be sub-saturated. While the equilibrium concentration of the drug in the two matrices depends on the ratio of layer thickness, the bi-layer system will always be at or below saturation. Thus, since each layer is sub-saturated and the layers are in equilibrium with each other, all layer-thickness combinations are sub-saturated. Therefore, the layer-thickness ratio can be selected to provide the desired transdermal delivery profile without exceeding solubility.

The ability to form devices that does not exceed solubility in any of the layers is particularly relevant in this aspect of the invention since this prevents the drug from recrystallizing in the matrix and minimizes stability concerns. Recrystallized drugs will generally comprise particles having a different size and shape compared to the non-recrystallized drug. These recrystallized drug particles will cause the composition of the invention to have a different and often non-preferred release profile. Further, recrystallization often occurs more readily at the surface of the matrix as solvent evaporates, creating a higher concentration of recrystallized drug at the surface of the adhesive and limiting the tackiness of the device and can also affect delivery. One additional advantage of the compositions where each of the layers are sub-saturated with drug is that devices with various thicknesses and thus various activities of the drug can be formed without being concerned about the stability of the composition.

Thus, in one specific embodiment, the composition of the invention contains a drug which is sub-saturated in each layer.

Figure 3A:
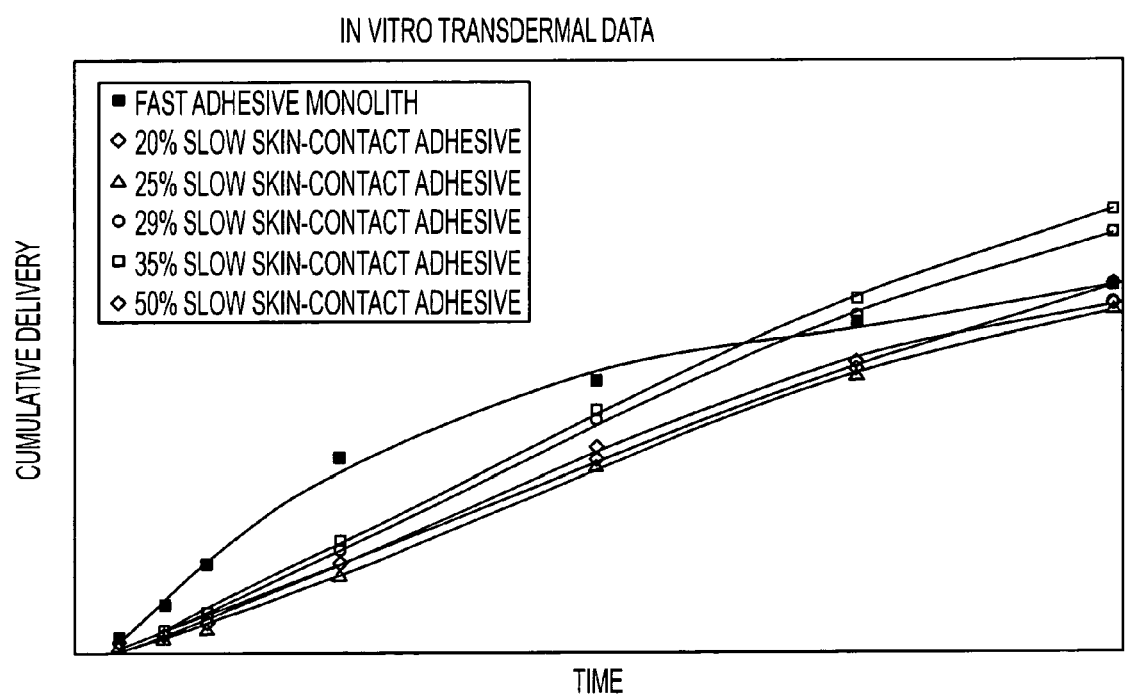
FIGS. 3a and 3b are graphs showing cumulative delivery for slow skin-contact adhesives adhesive bi-layers (i.e., the adhesive matrix having the slower initial rate of drug delivery is the skin contact layer).

In one specific embodiment, the composition has a slow skin-contact adhesive (i.e., in the bilayer system, the adhesive matrix having the slower initial rate of drug delivery is the skin contact layer and the adhesive matrix having the faster initial rate of drug delivery is the anchor layer) and the cumulative delivery of a drug is substantially linear over the delivery time, such as depicted by the bi-layer devices in FIG. 3a.

In one specific embodiment, the composition has a fast skin-contact adhesive (i.e., in the bilayer system, the adhesive matrix having the faster initial rate of drug delivery is the skin contact layer) and the drug flux rate comprises a delivery spike and then a steady-state flux. In one embodiment, the delivery spike has an intensity of at least 1.2 times the steady-state flux. In one embodiment, the delivery spike has an intensity of at least 1.5 times the steady-state flux.

The invention is further illustrated by the following examples, which are not to be construed as limiting.

EXAMPLES

Example 1

Preparation of a Two-Layer Delivery Device

Separate adhesive blends are made for each layer of the finished system, with the drug dissolved or suspended in at least one blend. The blends are made by suspending or dissolving the drug in a combination of solvent, adhesive, and, optionally, excipient. Desired remaining components for each blend can be dispersed in a premix or added directly to the adhesive blends along with the drug. Once all the components are added together in their respective blend, the blends are mixed separately with an air driven mixer until uniform. See Table 1 below for example amounts of each component blend:

TABLE 1

| Component | % (w/w) Wet | Weight (g) |
|---|---|---|
| Anchor Layer Blend | | |
| Ethyl Alcohol Dehydrated Alcohol USP-200 Proof punctilious (Ethyl Alcohol) | 4.56 | 9.50 |
| Estradiol Hemihydrate, USP, micronized | 0.63 | 1.32 |
| Povidone USP (Plasdone K-29/32) | 1.55 | 3.23 |
| DURO-TAK ® 87-2194 | 93.25 | 194.14 |
| Skin Contact Layer Blend | | |
| Ethyl Alcohol Dehydrated Alcohol USP-200 Proof punctilious (Ethyl Alcohol) | 5.89 | 6.00 |
| Estradiol Hemihydrate, USP, micronized | 0.81 | 0.83 |
| Povidone USP (Plasdone K-29/32) | 2.00 | 2.04 |
| 360 Medical Fluid (100 cSt.) | 2.94 | 3.00 |
| BIO-PSA ®7-4502 | 88.36 | 90.08 |

Following thorough mixing, the anchor layer blend is coated onto an appropriate release liner at the specified thickness to obtain the desired gsm. The laminate is dried for 4 minutes at 41° C. followed by 4 minutes at 77° C. in forced air ovens, then laminated to the desired backing film. The skin contact layer blend is coated onto a separate release liner and dried, using the same conditions as were used to prepare the anchor layer laminate.

To assemble the finished product, the anchor layer release liner is removed and the adhesive side of the dried skin contact layer is laminated to the adhesive side of the anchor layer.

Example 2

Transdermal delivery devices were made in accordance with the teachings of Example 1. Each device contained a total of 0.1-4.0% (w/w) drug. The anchor adhesive matrix of each delivery device was an acrylic pressure-sensitive adhesive and initially contained 0.1%-4.0% drug and between 0-5.0% (w/w) povidone. The skin contact matrix of each delivery device comprised a silicone pressure-sensitive adhesive and initially contained 0.1% to 4.0% of the drug, 0-5% (w/w) povidone and 0-5% of a tackifier/plasticizer. The silicone contact layer of each device had a thickness of 5-100 gsm and the anchor layer had a thickness of 5-150 gsm. In one embodiment, the device comprised 1.4% estradiol in each of the acrylic adhesive layer and the skin contact layer, 3.4% povidone in each of the acrylic adhesive layer and the skin contact layer, and the skin contact layer comprised 5% of 360 Medical Fluid (100 cSt) as the tackifier/plasticizer.

Example 3

Transdermal delivery devices were made in accordance with the teachings of Example 1. Each device contained a total of 0.1-4.0% (w/w) drug. The anchor adhesive matrix of each delivery device was an acrylic pressure-sensitive adhesive and initially contained 1.4% drug and between 0-5.0% (w/w) povidone. The anchor layer also contained 0-10% (w/w) propylene glycol. The skin contact matrix of each delivery device comprised a polyisobutylene pressure-sensitive adhesive and initially contained 1.0% drug, 0-5% (w/w) povidone and 10-50% of a tackifies/plasticizer. In each device, the skin contact layer had a thickness of 5-100 gsm and the anchor layer had a thickness of 5-100 gsm. In one embodiment, the device comprised 3.4% povidone in each of the acrylic adhesive layer and the skin contact layer, and the skin contact layer comprised 30% mineral oil as the tackifier/plasticizer.

Example 4

A transdermal device was made in accordance with the teachings of Example 2. The silicone skin contact layer had a thickness of 25 gsm and the anchor layer had a thickness of 75 gsm.

Example 5

A transdermal device was made in accordance with the teachings of Example 2. The silicone skin contact layer had a thickness of 50 gsm and the anchor layer had a thickness of 75 gsm.

Example 6

A transdermal delivery device was made in accordance with the teachings of Example 3. The polyisobutylene skin contact layer had a thickness of 50 gsm and the acrylate anchor layer had a thickness of 50 gsm.

Example 7

Transdermal delivery devices were made in accordance with the teachings of each of Examples 2 and 3. In each device, the drug was estradiol, a combination of estradiol and norethindrone acetate or a combination of estradiol and levonorgestrel.

Example 8

Transdermal delivery devices were made in accordance with the teachings of Example 2. In each device, the silicon adhesive was BIO-PSA® 7-4202, 7-4301, 7-4302, 7-4501, 7-4502 or 7-4602.

Example 9

Transdermal delivery devices were made in accordance with the teachings of Example 3. In each device, the polyisobutylene adhesive comprised from 20-80% of polyisobutylene with a molecular weight of at least 1,000,000 and 80-20% of polyisobutylene with a molecular weight of between 100 and 1,000,000.

Example 10

Transdermal delivery devices were made in accordance with the teachings of Example 9. In each device, the polyisobutylene adhesive comprised 45% polyisobutylene with a molecular weight of at least 1,000,000 and 55% polyisobutylene with a molecular weight of between 100 and 1,000,000.

Example 11

A transdermal delivery device was made in accordance with the teachings of Example 2. The 50 gsm skin contact layer contained 1.4% estradiol hemihydrate, 3.4% povidone and 5% 360 Medical Fluid (100 cSt) in a medical grade, silicone pressure sensitive adhesive BIO-PSA® 7-4502. The 75 gsm anchor layer contained 1.4% estradiol hemihydrate and 3.4% povidone in DURO-TAK® 87-2194, a medical grade acrylate pressure sensitive adhesive. The backing consisted of polyolefin (MEDIFLEX® 1000). The release liner was fluorosilicone coated polyester (MEDIRELEASE® 2500 or Scotchpak® 1022). All percentages are w/w.

The delivery system had a size of 30 cm$^2$, produced a delivery spike of estradiol and delivered approximately 0.1 mg/day in vitro.

Example 12

A transdermal delivery device was made in accordance with the teachings of Example 3. The 50 gsm skin contact layer contained 1.0% estradiol hemihydrate, 3.4% povidone and 30% mineral oil in medical grade polyisobutylene pressure sensitive adhesive. The 50 gsm anchor layer contained 1.37% estradiol hemihydrate, 8.0% propylene glycol and 3.4% povidone in DURO-TAK® 87-2194, a medical grade acrylate pressure sensitive adhesive. The backing consisted of polyolefin (MEDIFLEX® 1000). The release liner was siliconized polyester (MEDIRELEASE® 2249). All percentages are given on a w/w basis.

The delivery device had a size of 30 cm$^2$, produced a delivery spike of estradiol and delivered 0.1 mg/day in vitro.

Example 13

A transdermal delivery device was made in accordance with the teachings of Example 1. The anchor layer matrix comprised 50 gsm DURO-TAK® 87-2194 to which was laminated a 50 gsm polyisobutylene skin contact layer matrix. The anchor layer matrix contained 1.37% estradiol hemihydrate, 4.0% propylene glycol, 3.4% povidone and 1.13% colloidal silicon dioxide. The skin contact layer matrix contained 1.37% estradiol hemihydrate, 3.4% povidone, 4.0% propylene glycol, 1.13% colloidal silicon dioxide, and 30% mineral oil in a polyisobutylene adhesive. The backing was MEDIFLEX® 1000 and the release liner was MEDIRELEASE® 2226.

Example 14

A transdermal delivery device was made in accordance with the teachings of Example 1. The anchor layer matrix comprised 75 gsm DURO-TAK® 87-2194 to which was laminated a 50 gsm skin contact layer matrix of BIO-PSA® 7-4502. The anchor layer matrix contained 1.37% estradiol hemihydrate and 3.4% povidone. The skin contact layer matrix contained 1.37% estradiol hemihydrate, 3.4% povidone and 5% 360 Medical Fluid (100 cSt). The backing was MEDIFLEX® 1000 and the release liner was MEDIRELEASE® 2500.

Example 15

A delivery device was made in which the rate of delivery of drug from the skin contact layer was slower than the rate of release from the anchor layer. The transdermal delivery profiles of the bilayer and constitutive monolayers show that the bi-layer delivers drug through the skin at the same normalized rate as the rapidly delivering (silicone) matrix, but at a steady rate characteristic of the slow-delivery (acrylic) matrix.

Rapidly delivering adhesive films were prepared by coating a silicone adhesive blend so as to create a homogeneous dry adhesive layer containing 1.25% estradiol, 5% polyvinyl pyrrolidone, 4% oleic acid, and BIO-PSA® 7-4502 silicone adhesive. The blend was coated onto 3M ScotchPak® 1022 release liner and dried for 4 minutes at 41° C. and 4 minutes at 77° C. to create adhesive films of approximately 100 grams per square meter (gsm).

Slowly delivering adhesive films were prepared by coating an acrylic adhesive blend so as to create a homogeneous dry adhesive layer containing 1.25% estradiol, 5% polyvinyl pyrolidone, 4% oleic acid and DURO-TAK® 87-2516 acrylic adhesive from National Starch and Chemical Co. The blend was coated onto MEDIRELEASE® 2249 release liner and dried for 4 minutes at 40° C. and 4 minutes at 77° C. to create two dry adhesive films of approximately 25 and 100 gsm, respectively.

Two drug delivery systems were prepared by laminating either the 100 gsm rapidly delivering silicone adhesive film or the 100 gsm slowly delivering acrylic adhesive film to 3M CoTran 9722 backing film.

A third drug delivery system was prepared by first transferring the rapidly delivering silicone adhesive film from the release liner to 3M CoTran 9722 backing film. The 25 gsm slowly delivering acrylic adhesive film was laminated on top of the rapidly delivering silicone adhesive film. The finished system consisted of a backing film, 100 gsm silicone adhesive layer, 25 gsm acrylic adhesive layer and release liner. After allowing all systems to equilibrate, they were tested for in vitro delivery of drug through human skin. The table below summarizes the three systems tested:

| System 1 (Rapidly Delivering Silicone Adhesive Matrix) | System 2 (Slowly Delivering Acrylic Matrix) | System 3 (Bi-Layer with Slowly Delivering Acrylic Matrix in Contact with Skin) |
|---|---|---|
| GSM: 100 | GSM: 100 | Acrylic GSM: 25 Silicone GSM: 100 |
| Estradiol 1.25% | Estradiol 1.25% | Estradiol 1.25% |
| PVP 5% | PVP 5% | PVP 5% |
| Oleic Acid 4% | Oleic Acid 4% | Oleic Acid 4% |

Figure 2:
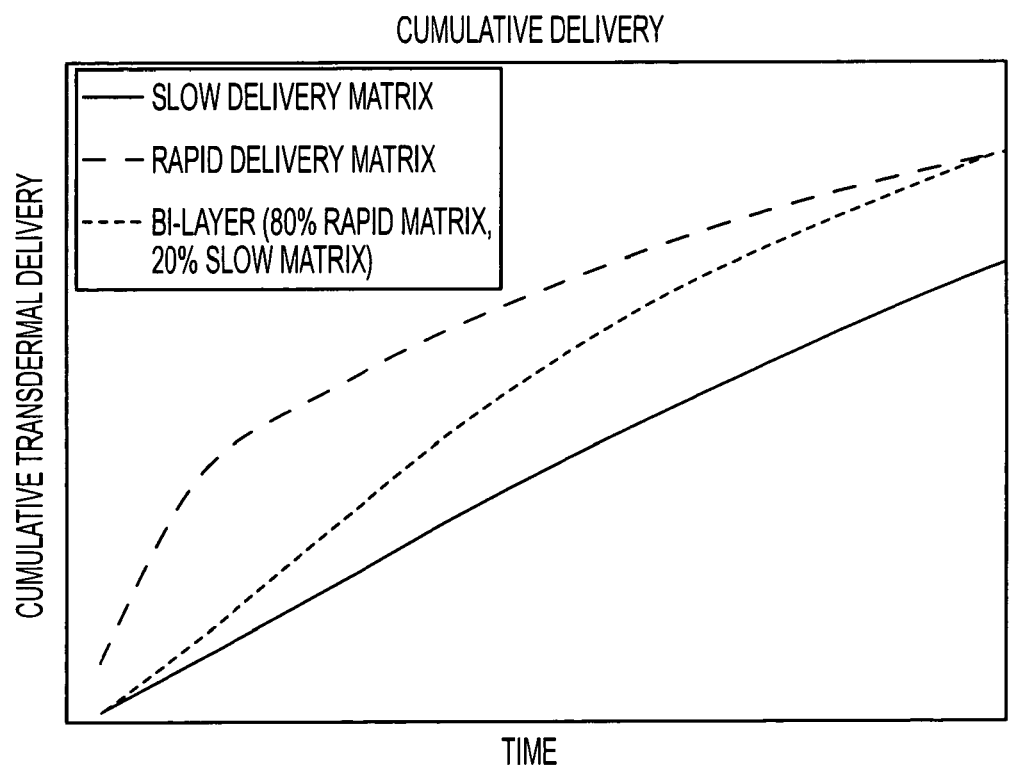
FIG. 2 is a graph showing the cumulative delivery of the three matrices of FIG. 1.

By laminating the two layers together, the resulting transdermal system delivered the medication through the skin at the same normalized rate as the rapidly-delivering matrix, but at a steady continuous rate more characteristic of the slowly-delivering matrix. See FIGS. 1 and 2.

Example 16

Bi-layer transdermal devices were made in accordance with the teachings of Example 1. Devices using a slower adhesive as the skin-contact layer and the faster adhesive as the anchor layer (the slow skin-contact adhesive bi-layer) as well as devices using the faster adhesive as the skin-contact layer and the slower adhesive as the anchor layer (the fast skin-contact adhesive bi-layer) were made. For comparison, single layer (monolithic) transdermal devices were also made in accordance with this teaching.

The drug delivery devices were adhered to the stratum corneum of heat-split human cadaver epidermis and mounted in a horizontal diffusion chamber. The devices used in this study had a 2 $cm^2$ diffusion area and at least three replicates were performed for each formulation/donor combination. The temperature of the receptor solution was kept at 32° C. with constant stirring. The receptor solution (normal saline with 0.015% $NaN_3$) was collected and analyzed for drug concentration by HPLC at predetermined intervals to calculate the cumulative amount of drug delivered at each time point and the average flux between time points.

Figure 3B:
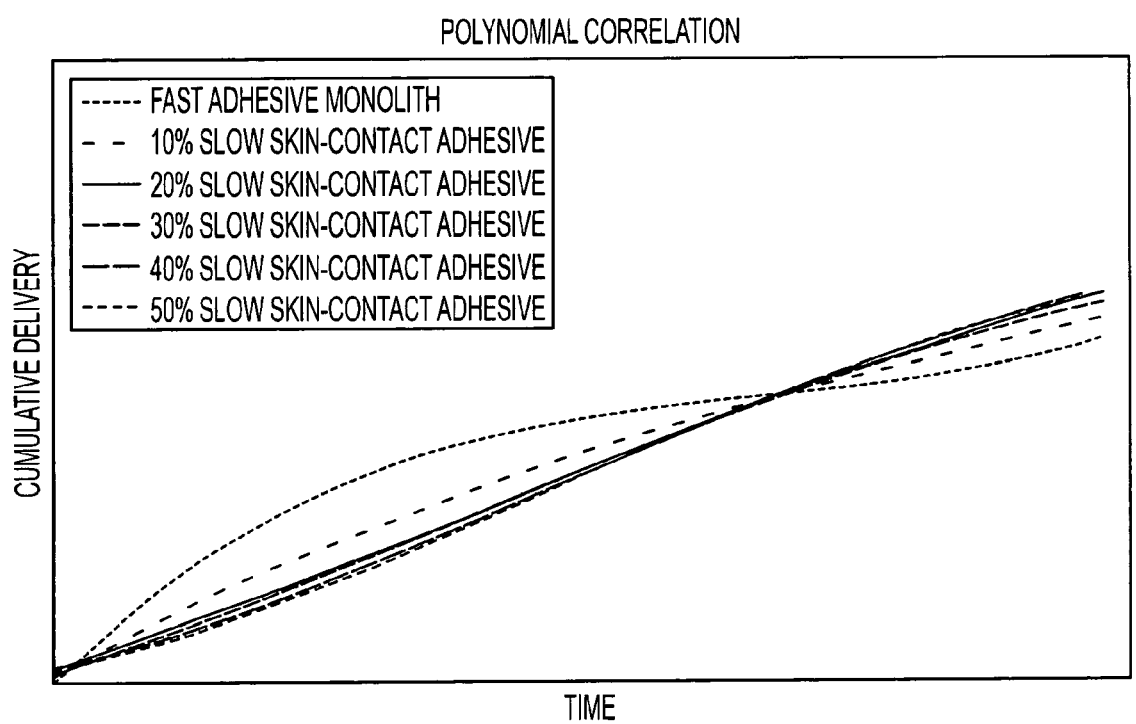
Figure 4A:
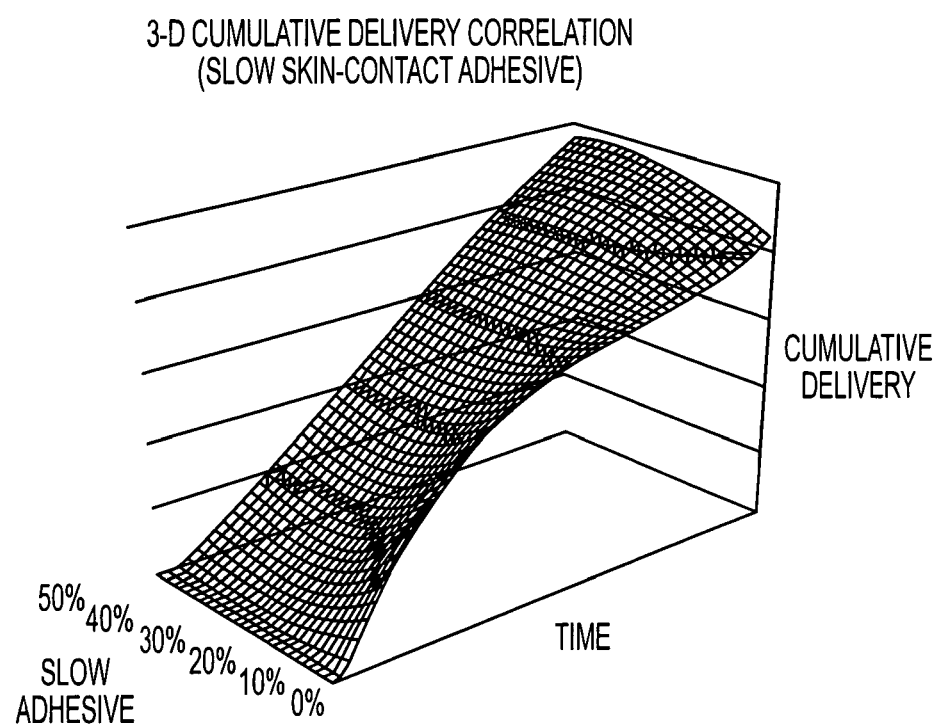
FIGS. 4a and 4b are 3-dimensional correlation graphs for slow skin-contact adhesive bi-layers.
Figure 4B:
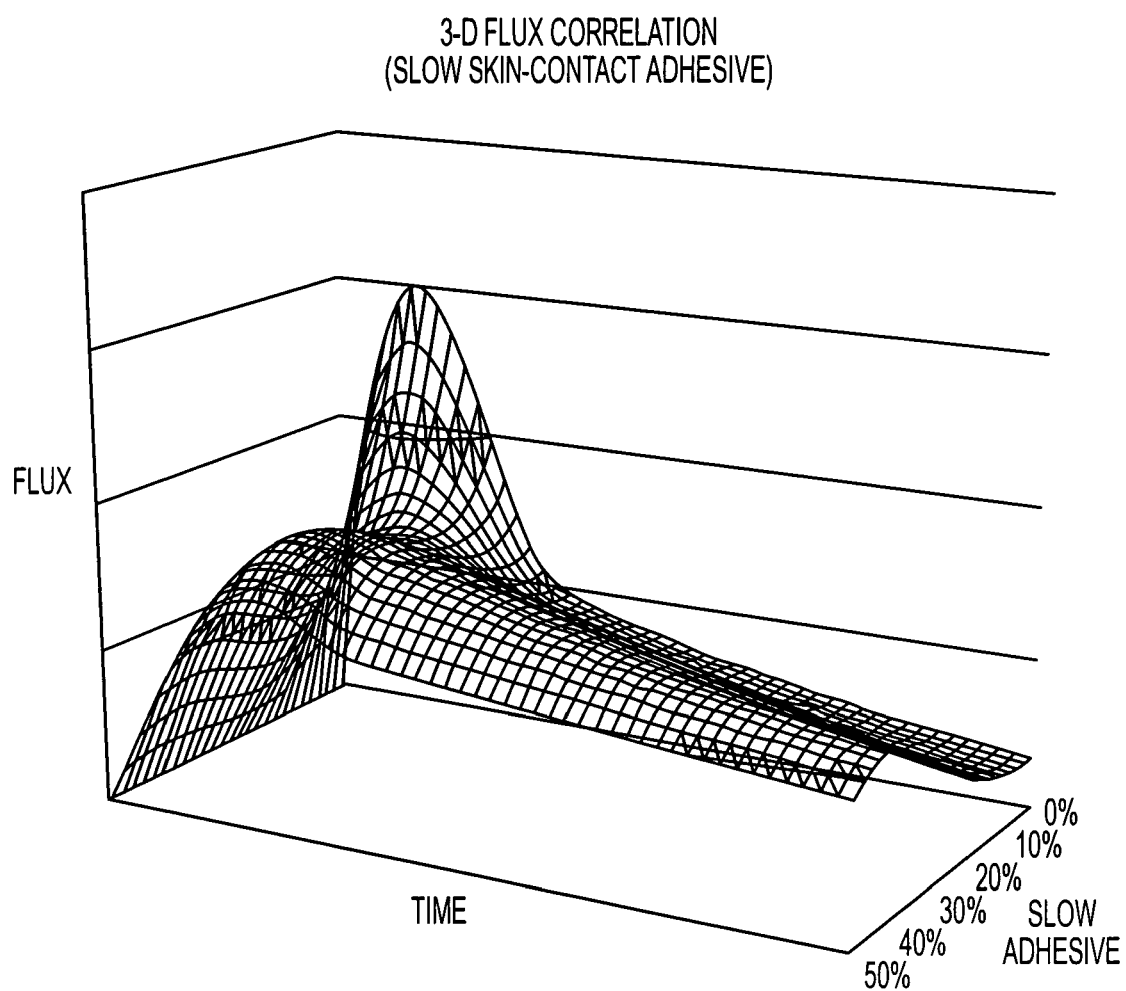

FIGS. 3a and 3b provide the results for devices having a slow-skin contact adhesive. Using the slower adhesive as the skin-contact layer limits the delivery spike associated with a monolith made from a faster delivering adhesive. Varying the thickness ratio between the two layers between 10% and 50% allowed tuning of the delivery spike relative to the steady-state flux. FIGS. 4a and 4b provide a three-dimensional view of both the cumulative delivery and flux for the fast adhesive and the fast adhesive anchor layer having up to 50% slow skin-contact adhesive. The slow skin-contact adhesive spreads out the flux spike characteristic of the faster adhesive resulting in a higher steady-state flux than either adhesive can achieve as a monolith.

Figure 5A:
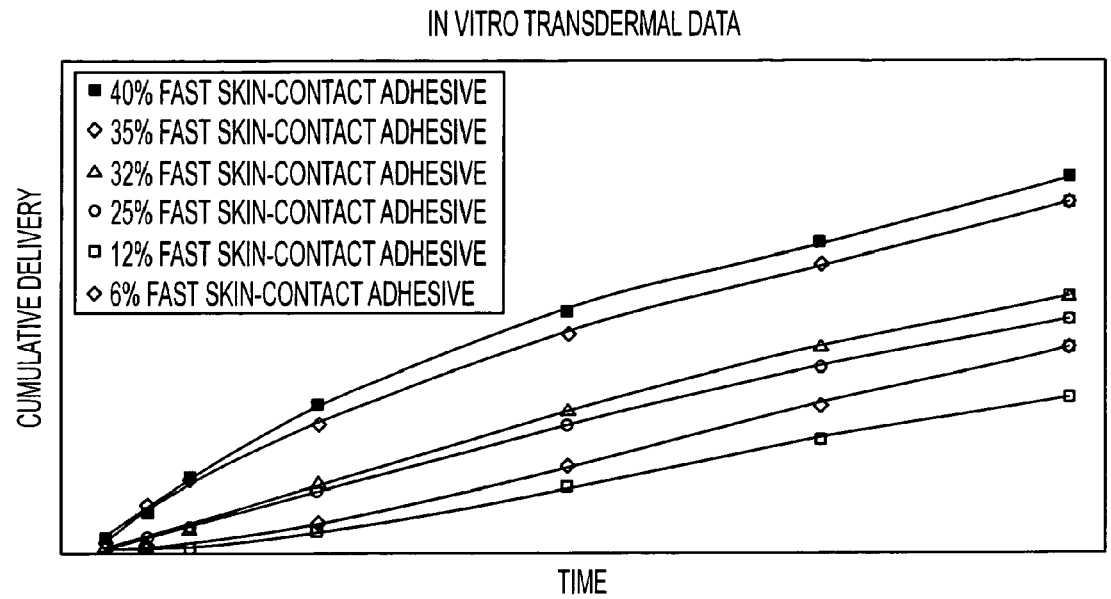
FIGS. 5a and 5b are graphs showing cumulative delivery for fast skin-contact adhesives adhesive bi-layers (i.e., the adhesive matrix having the faster initial rate of drug delivery is the skin contact layer).
Figure 5B:
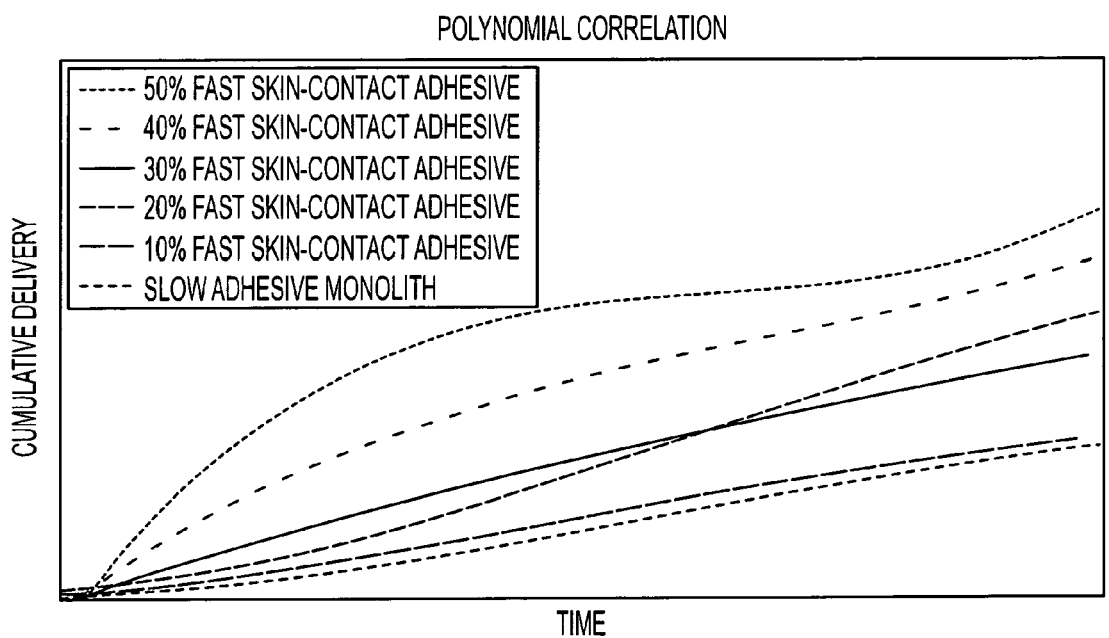
Figure 6A:
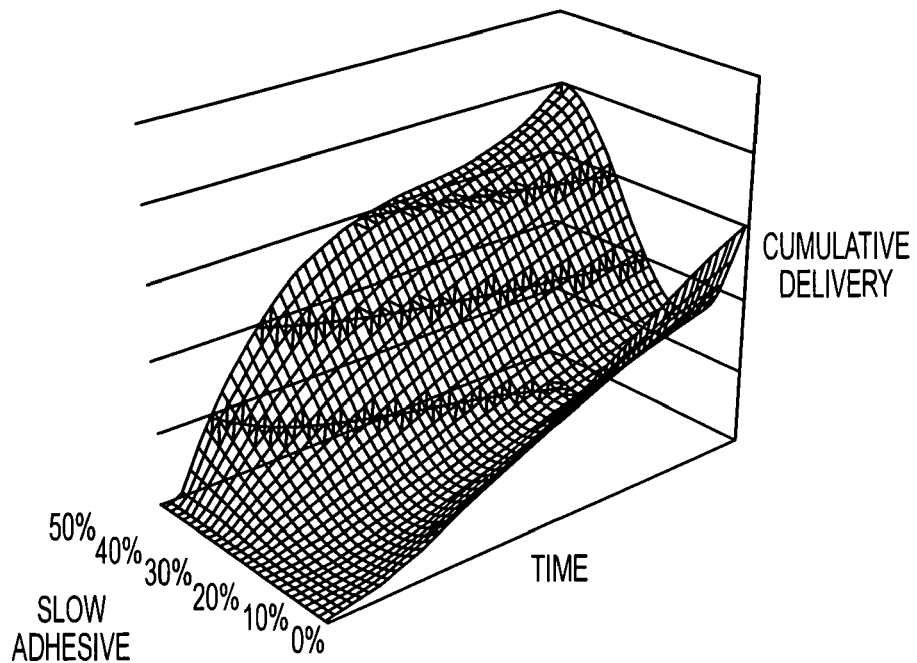
FIGS. 6a and 6b are 3-dimensional correlation graphs for fast skin-contact adhesive bi-layers.
Figure 6B:
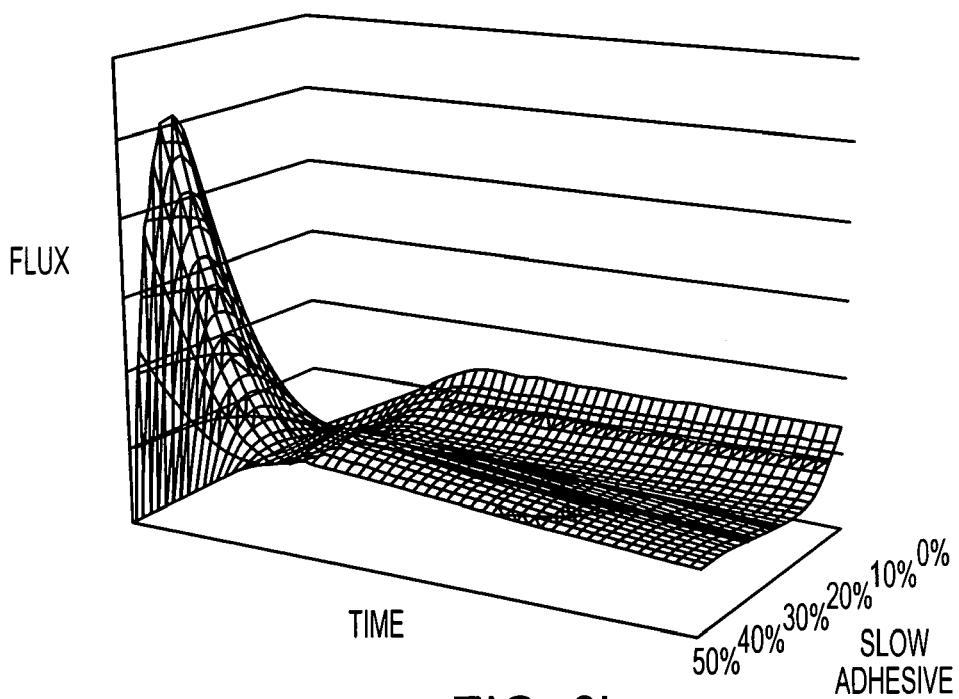

FIGS. 5a and 5b provide the results for devices having a fast skin contact adhesive. Using a faster adhesive as the skin-contact layer creates a variable delivery spike without sacrificing the long-term steady-state delivery associated with a monolith made from a slower delivering adhesive. Varying the thickness ratio between the two layers between 10% and 50% allows tuning of the delivery spike while retaining the long-term steady-state flux associated with the slower adhesive. FIGS. 6a and 6b provide a three-dimensional view of both the cumulative delivery and flux for the slow adhesive and for the slow adhesive anchor layer with up to 50% fast skin-contact adhesive. The fast skin-contact adhesive creates a variable bolus or priming dose followed by the long-term steady-state flux characteristic of the slower adhesive.

Figure 7:
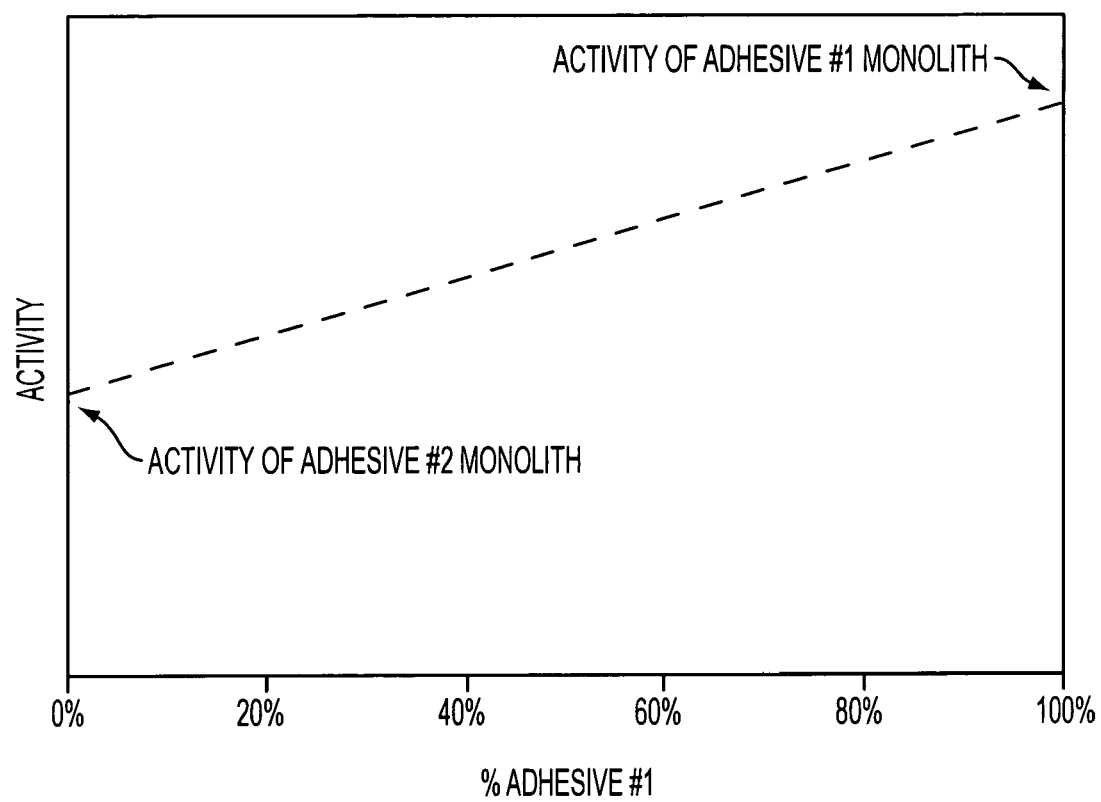
FIG. 7 shows the thermodynamic activity of a bi-layer system of varying layer thickness ratio relative to its constituent monoliths at a constant average concentration.

FIG. 7 demonstrates the linear relationship of the total activity of the adhesives in the monolith as the relative amount of each adhesive in the devices is changed at constant average concentration.

The invention claimed is:

1. A method for making a transdermal drug-containing dosage unit which comprises a laminate comprising:
   contacting a backing layer substantially impervious to a drug to be delivered transdermally; with
   a first polymeric adhesive matrix, having dispersed therein a drug and having a first initial rate of delivery of the drug;
   contacting the first polymeric adhesive matrix with a second polymeric adhesive matrix, having dispersed therein the drug and having a second initial rate of delivery of the drug, wherein said second initial rate of delivery is different from said first initial rate of delivery; and
   contacting the second polymeric adhesive matrix with a release liner.

2. The method of claim 1, wherein said first polymeric adhesive matrix delivers said drug more slowly than said second polymeric adhesive matrix.

3. The method claim 1, wherein said second polymeric adhesive matrix delivers said drug more slowly than said first polymeric adhesive matrix.

4. The method of claim 1, wherein one of said first and second adhesive matrices has an initial delivery rate of a given amount of said drug that is at least about 10% faster than that of the other of said adhesive matrices.

5. The method of claim 1, wherein either said first or said second polymeric adhesive matrix comprises an acrylic adhesive.

6. The method of claim 1, wherein said first adhesive matrix comprises an acrylic adhesive and said second adhesive matrix comprises a silicone adhesive.

7. The method of claim 1, wherein said first adhesive matrix comprises an acrylic adhesive and said second adhesive matrix comprises a polyisobutylene adhesive.

8. The method of claim 6, wherein said silicone adhesive comprises a standard silicone adhesive or an amine compatible silicone adhesive.

9. A method for making a transdermal drug-containing dosage unit which comprises a laminate comprising:
   contacting a backing layer substantially impervious to the drug to be delivered transdermally with a first polymeric adhesive matrix, having dispersed therein a drug and having a first initial rate of delivery of the drug;

contacting a second polymeric adhesive matrix, having dispersed therein the drug and having a second initial rate of delivery of the drug with the first adhesive matrix;

contacting a third polymeric adhesive matrix, having dispersed therein the drug and having a third initial rate of delivery of the drug with the second adhesive matrix; and contacting a release liner with the third polymeric adhesive matrix;

wherein said initial rates of delivery of at least two of said matrices are different from one another.

10. The method of claim 9, which further comprises contacting at least one additional drug-containing polymeric adhesive matrix with said first and second polymeric adhesive matrices.

11. The method of claim 9, wherein each of said first, second and third initial rates of delivery is different from said other initial rates of delivery.

12. The method of claim 9, wherein either said first and third adhesive matrices or said second adhesive matrix comprises an acrylic adhesive.

13. The method of claim 1, wherein said drug comprises a cardiovascular drug, an androgenic steroid, an estrogen, a progestational agent, a drug which acts on the central nervous system, a nutritional agent, an anti-inflammatory agent, an antihistamine, a miotic, a dermatological agent, an anti-spasmodic, an anti-depressant, an anti-cancer drug, an anti-diabetic, an anti-estrogen, an anti-psychotic, an anti-infective agent, an anti-allergenic, an anti-pyretic, an anti-migraine agent or a tranquilizer.

14. The method of claim 1, wherein said drug comprises an estrogen or a combination of an estrogen and a progestin.

15. The method of claim 14, wherein said estrogen comprises estradiol or mono- or di-esters thereof which are transdermally absorbable.

16. The method of claim 14 wherein said progestin comprises norethindrone acetate or levonorgestrel.

17. The method of claim 1 wherein the transdermal drug-containing dosage unit comprises from about 0.1% to about 4.0% w/w of the drug.

18. The method of claim 14 wherein the transdermal drug-containing dosage unit comprises from about 0.1% to about 4.0% of said estrogen.

19. The method of claim 18 wherein the transdermal drug-containing dosage unit further comprises from about 0.1% to about 20% of the progestin.

\* \* \* \* \*